United States Patent
Yokosawa

(10) Patent No.: US 10,980,747 B2
(45) Date of Patent: Apr. 20, 2021

(54) COMPOSITION FOR SOLID PREPARATION, SOLID PREPARATION, AND METHOD FOR PRODUCING THE SAME

(71) Applicant: SHIN-ETSU CHEMICAL CO., LTD., Tokyo (JP)

(72) Inventor: Takuya Yokosawa, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 16/193,415

(22) Filed: Nov. 16, 2018

(65) Prior Publication Data

US 2019/0160012 A1    May 30, 2019

(30) Foreign Application Priority Data

Nov. 27, 2017  (JP) .............................. JP2017-226632
Oct. 25, 2018  (JP) .............................. JP2018-201004

(51) Int. Cl.
| | | |
|---|---|---|
| *A61K 9/20* | (2006.01) | |
| *A61K 31/522* | (2006.01) | |
| *A61K 9/28* | (2006.01) | |
| *A61K 47/38* | (2006.01) | |
| *A61K 31/52* | (2006.01) | |

(52) U.S. Cl.
CPC .......... *A61K 9/2054* (2013.01); *A61K 9/2095* (2013.01); *A61K 9/2866* (2013.01); *A61K 31/522* (2013.01); *A61K 47/38* (2013.01); *A61K 31/52* (2013.01)

(58) Field of Classification Search
CPC .. A61K 9/2054; A61K 9/2095; A61K 9/2866; A61K 31/522; A61K 47/38; A61K 31/52
See application file for complete search history.

(56) References Cited

U.S. PATENT DOCUMENTS

| | | | |
|---|---|---|---|
| 5,009,895 A | 4/1991 | Lui | |
| 9,408,836 B2 * | 8/2016 | Armendariz Borunda | ................ A61K 9/2054 |
| 9,980,946 B1 * | 5/2018 | Rizk | ................ A61K 9/2054 |
| 2005/0095292 A1 * | 5/2005 | Benjamin | ............ A61K 9/2866 424/468 |
| 2014/0296300 A1 * | 10/2014 | Armendariz Borunda | ................ A61P 29/00 514/345 |
| 2020/0038386 A1 * | 2/2020 | Armendariz Borunda | ................ A61K 31/4412 |

FOREIGN PATENT DOCUMENTS

| | | |
|---|---|---|
| JP | H06-305982 A | 11/1994 |
| JP | 2015-227909 A | 12/2015 |

OTHER PUBLICATIONS

Mar. 27, 2019 Search Report issued in European Patent Application No. 18208161.2.

* cited by examiner

*Primary Examiner* — Robert A Wax
*Assistant Examiner* — Olga V. Tcherkasskaya
(74) *Attorney, Agent, or Firm* — Oliff PLC

(57) ABSTRACT

A composition which is used for the production of a solid preparation exhibiting a small variation of dissolution even at a low content of hydroxypropyl methyl cellulose (HPMC), and others. More specifically, provided are a composition for a solid preparation, the composition including HPMC having a polydispersity of 4.0 or more, as determined by absolute molecular weight measurement, and having a viscosity at 20° C. of 1,500 to 15,0000 mPa·s, as determined in a 2% by mass aqueous solution thereof, and an active ingredient; the solid preparation including the composition; and a method for producing a tablet including a step of dry-mixing said HPMC with an active ingredient to obtain a mixture, or granulating a mixture including said HPMC and an active ingredient to obtain a granulated product, and a step of tableting the mixture or the granulated product to obtain a tablet.

11 Claims, No Drawings

COMPOSITION FOR SOLID PREPARATION, SOLID PREPARATION, AND METHOD FOR PRODUCING THE SAME

BACKGROUND OF THE INVENTION

1. Field of the Invention

The present invention relates to a composition for a solid preparation, a solid preparation, and a method for producing the solid preparation.

2. Description of the Related Art

A solid preparation is easy to administer and thus is widely used. Specifically, a sustained-release preparation is useful because it can control the concentration of an active ingredient dissolved in the blood at a certain level or less, or reduce the number of administrations. The sustained-release preparation is roughly classified into a single unit type preparation and a multiple unit type preparation.

The single unit type preparation gradually discharges an active ingredient to exhibit sustained-release characteristics, while maintaining the dosage form thereof in the gastrointestinal tract, and is produced by tableting a mixture with a water-soluble polymer or a wax. The single unit type preparation includes a matrix type preparation. In contrast, the multiple unit type preparation is a tablet or an encapsulated formulation, and is immediately disintegrated on administration to discharge granules having an active ingredient coated with a polymer film, and exhibits sustained-release characteristics.

The matrix type sustained-release preparation is produced by a simple method, and the dissolution thereof is easily controlled. Hence, the matrix type sustained-release preparation is one of the most widely used sustained-release preparations. Of the matrix type sustained-release preparations, for example, a gel matrix type sustained-release preparation contains hydroxypropyl methyl cellulose (hereinafter also called "HPMC") which is a nonionic water-soluble polymer.

For the matrix type sustained-release preparation containing HPMC, the reproducibility in dissolution test of the preparation is crucially important, and the preparation is required to be designed to exhibit high reproducibility of dissolution test or to have a small variation in dissolution. It is typically known that a preparation containing a larger amount of HPMC gives a smaller dissolution variation. However, such a tablet has a larger size so that it is inferior in administration. Thus, the content of HPMC is preferably smaller. On the other hand, a tablet containing a smaller amount of HPMC may fail to stably form a matrix, so that it is possible to have a larger variation in dissolution when subjected to dissolution test.

Examples of the sustained-release preparation containing HPMC include a sustained-release preparation containing HPMC particles having a particular substitution degree and particular powder properties (JP H06-305982A) and a sustained-release preparation containing high-viscosity HPMC and low-viscosity HPMC and exhibiting a zero-order release state (JP 1107-053364A).

SUMMARY OF THE INVENTION

JP H06-305982A discloses that the sustained-release preparation containing HPMC is shown to have a controlled dissolution rate, but there is no suggestion about dissolution variations. JP H07-053364A discloses that the sustained-release preparation containing high-viscosity HPMC and low-viscosity HPMC at a certain ratio is suggested to show the zero-order release state, but there is no suggestion about dissolution variations. In addition, an HPMC mixture containing the high-viscosity HPMC and the low-viscosity HPMC at the ratio disclosed in JP H07-053364A has a low viscosity, so that a tablet is required to have a higher HPMC content in order to achieve preferred dissolution behavior. However, this leads to a larger tablet size, and such a large tablet is unfavorably inferior in administration.

An object of the invention is to provide a composition comprising HPMC and an active ingredient, the composition being able to produce a solid preparation exhibiting a small variation of dissolution even at a low content of the HPMC; the solid preparation; and a method for producing the solid preparation.

As a result of intensive studies, the inventors have found that a composition for a solid preparation, the composition comprising HPMC and an active ingredient, can solve the above problems, wherein the HPMC has a polydispersity of 4.0 or more, as determined by absolute molecular weight measurement, and a viscosity at 20° C. of 1,500 to 150,000 mPa·s, as determined in a 2% by mass aqueous solution thereof; and have completed the invention.

In an aspect of the invention, there is provided a composition for a solid preparation, the composition comprising:

HPMC having a polydispersity of 4.0 or more, as determined by absolute molecular weight measurement, and a viscosity at 20° C. of 1,500 to 15,0000 mPa·s, as determined in a 2% by mass aqueous solution; and an active ingredient.

In another aspect of the invention, there is provided a solid preparation comprising the composition for a solid preparation.

In still another aspect of the invention, there is provided a method for producing a tablet, comprising steps of:

dry-mixing HPMC having a polydispersity of 4.0 or more, as determined by absolute molecular weight measurement, and a viscosity at 20° C. of 1,500 to 150,000 mPa·s, as determined in a 2% by mass aqueous solution, with an active ingredient to obtain a mixture; and tableting the mixture to obtain a tablet.

In still another aspect of the invention, there is provided a method for producing a tablet, comprising steps of:

granulating a mixture comprising HPMC having a polydispersity of 4.0 or more, as determined by absolute molecular weight measurement, and a viscosity at 20° C. of 1,500 to 150,000 mPa·s, as determined in a 2% by mass aqueous solution, and an active ingredient to obtain a granulated product; and tableting the granulated product to give a tablet.

According to the invention, a solid preparation containing a smaller amount of HPMC and exhibiting a smaller variation of dissolution of an active ingredient can be produced.

DETAILED DESCRIPTION OF THE PREFERRED EMBODIMENTS

First, HPMC to be used in a composition for a solid preparation will be described.

The HPMC to be used in a composition for a solid preparation has a polydispersity of 4.0 or more, preferably 4.0 to 20.0, more preferably 5.0 to 17.0, even more preferably 7.0 to 17.0, as determined by absolute molecular weight measurement. When the HPMC has a polydispersity of less than 4.0, the variation of dissolution becomes large.

The polydispersity is defined as the ratio (Mw/Mn) of a weight-average molecular weight (Mw) to a number-average molecular weight (Mn), and represents the spread of molecular weights (molecular weight distribution). A smaller value of Mw/Mn shows a narrower molecular weight distribution, while a larger value of Mw/Mn shows a wider molecular weight distribution.

The weight-average molecular weight (Mw) and the number-average molecular weight (Mn) may be determined by absolute molecular weight measurement using size exclusion chromatography (SEC) and multi-angle laser light scattering (MALLS) in combination (Tablets & Capsules, 14-20, July 2007).

Various methods of determining the molecular weight of the HPMC have been reported, and examples thereof include relative molecular weight determination by SEC described in Journal of Pharmacy and Pharmacology, Vol. 32, 116-119 (1980), absolute molecular weight measurement by combination of SEC and low angle laser light scattering (LALLS) described in Kobunshi Ronbunshu (Japanese Journal of Polymer Science and Technology), Vol. 39, No. 4, 293-298 (1982), and absolute molecular weight measurement by combination of SEC and MALLS described in Tablets & Capsules, 14-20, July 2007.

The relative molecular weight determination by SEC insufficiently eliminates the effect of HPMC molecular association so that it is indicated to give a higher value than an actual polydispersity (Mw/Mn). In contrast, the absolute molecular weight measurement by combination of SEC and LALLS and the absolute molecular weight measurement by combination of SEC and MALLS scarcely cause the above problem and thus are preferred. The absolute molecular weight measurement by combination of SEC and MALLS is more preferred from the viewpoint of a simpler measurement method and highly accurate molecular weight determination. Hence, the invention adopts the absolute molecular weight measurement by combination of SEC and MALLS.

The HPMC to be used in the composition for a solid preparation preferably has a weight-average molecular weight (Mw) of 200,000 to 800,000, more preferably 250,000 to 700,000, as determined by absolute molecular weight measurement, from the viewpoint of dissolution control of an active ingredient.

The HPMC to be used in the composition for a solid preparation preferably has a number-average molecular weight (Mn) of 10,000 to 200,000, more preferably 15,000 to 150,000, as determined by absolute molecular weight measurement, from the viewpoint of dissolution control of an active ingredient.

A 2% by mass aqueous solution of the HPMC to be used in the composition for a solid preparation has a viscosity at 20° C. of 1,500 to 150,000 mPa·s, preferably 2,000 to 100,000 mPa·s, more preferably 3,500 to 80,000 mPa·s. When the HPMC has the viscosity of less than 1,500 mPa·s, the HPMC is poor with respect to the effect of suppressing the dissolution of an active ingredient, for example, in a tablet containing a small content of the HPMC as a sustained-release preparation. When the HPMC has the viscosity of more than 150,000 mPa·s, the HPMC is excellent with respect to the effect of suppressing the dissolution, but is inferior with respect to the dissolution of an active ingredient.

When the viscosity at 20° C. of a 2% by mass aqueous solution of HPMC is less than 600 mPa·s, the viscosity may be determined in accordance with "Viscosity measurement by capillary tube viscometer" in "Viscosity Determination" of "General Tests" described in the Japanese Pharmacopoeia Seventeenth Edition, by using an Ubbelohde-type viscometer. When the viscosity determined by an Ubbelohde viscometer is 600 mPa·s or more, the viscosity may be determined by using MCR301, which is a rheometer produced by Anton Paar.

The HPMC to be used in the composition for a solid preparation may have any substitution degree of methoxy group, but from the viewpoint of dissolution control of an active ingredient, the substitution degree of methoxy group is preferably 14.0 to 32.0% by mass, more preferably 16.5 to 30.0% by mass, even more preferably 19.0 to 30.0% by mass, and particularly preferably 19.0 to 24.0% by mass.

The HPMC to be used in the composition for a solid preparation may have any substitution degree of hydroxypropoxy group, but from the viewpoint of dissolution control of an active ingredient, the substitution degree of hydroxypropoxy group is preferably 3.0 to 32.0% by mass, more preferably 3.0 to 12.0% by mass, even more preferably 4.0 to 12.0% by mass, and particularly preferably 8.5 to 10.5% by mass.

The substitution degrees of methoxy group and hydroxypropoxy group may be determined by a method in accordance with the measurement method of substitution degree for hydroxypropyl methyl cellulose (hypromellose) described in the Japanese Pharmacopoeia Seventeenth Edition.

The substitution type of the HPMC includes 1828 (a substitution degree of methoxy group of 16.5 to 20.0% by mass and a substitution degree of hydroxypropoxy group of 23.0 to 32.0% by mass), 2208 (a substitution degree of methoxy group of 19.0 to 24.0% by mass and a substitution degree of hydroxypropoxy group of 4.0 to 12.0% by mass), 2906 (a substitution degree of methoxy group of 27.0 to 30.0% by mass and a substitution degree of hydroxypropoxy group of 4.0 to 7.5% by mass), and 2910 (a substitution degree of methoxy group of 28.0 to 30.0% by mass and a substitution degree of hydroxypropoxy group of 7.0 to 12.0% by mass) described in "hypromellose" in the Japanese Pharmacopoeia Seventeenth Edition. From the viewpoint of dissolution control of an active ingredient, the substitution type 2208 or 2910 is preferred.

The HPMC to be used in the composition for a solid preparation has a volume-based average particle size of preferably 20 to 200 μm, more preferably 40 to 150 μm, even more preferably 50 to 100 μm, particularly preferably 60 to 90 μm, as determined by dry laser diffractometry, from the viewpoint of dissolution control of an active ingredient in a sustained-release preparation.

The average particle size may be determined by dry laser diffractometry using MASTERSIZER 3000 manufactured by Malvern in England or HEWS manufactured by Sympatec in Germany by the method comprising steps of: applying a laser beam to a powder sample sprayed by compressed air to measure diffraction intensities, and calculating the volume-based average particle size by using the diffraction intensities.

The HPMC to be used in the composition for a solid preparation may be mono-batch HPMC obtained from one batch, or a multi-batch HPMC mixture obtained from two or more batches, for example, an HPMC mixture containing low-viscosity HPMC obtained from a batch and high-viscosity HPMC obtained from another batch (hereinafter, "mono-batch HPMC", "low-viscosity HPMC" and "high-viscosity HPMC" are also called "material HPMC").

The mono-batch HPMC can be produced by subjecting a pulp mixture comprising low-polymerization-degree pulp and high-polymerization-degree pulp to a known method for producing HPMC. In other words, the mono-batch HPMC having a polydispersity of 4.0 or more, as determined by absolute molecular weight measurement, and a viscosity at 20° C. of 1,500 to 150,000 mPa·s, as determined in a 2% by mass aqueous solution thereof, may be produced by the method comprising steps of: bringing a pulp mixture comprising low-polymerization-degree pulp and high-polymerization-degree pulp into contact with an alkali metal hydroxide solution to obtain alkali cellulose; and reacting the alkali cellulose with an etherifying agent. Preferably, a pulp mixture consisting essentially of low-polymerization-degree pulp and high-polymerization-degree pulp may be used.

The low-polymerization-degree pulp preferably has an intrinsic viscosity of 300 to 700 ml/g, more preferably 330 to 630 ml/g, even more preferably 330 to 510 ml/g, and particularly preferably 330 to 410 ml/g from the viewpoint of reduction in dissolution variation of an active ingredient. The high-polymerization-degree pulp preferably has an intrinsic viscosity of 750 to 2,500 ml/g, more preferably 850 to 2,000 ml/g, even more preferably 1,200 to 2,000 ml/g, and particularly preferably 1,400 to 2,000 ml/g from the viewpoint of reduction in dissolution variation of an active ingredient. The intrinsic viscosities of the low-polymerization-degree pulp and the high-polymerization-degree pulp may be determined by using an Ubbelohde viscometer in accordance with the viscosity measurement method described in "7. Method B: measurement of intrinsic viscosity at a constant shear rate" of HS P8215: 1998.

The ratio of the intrinsic viscosity of the high-polymerization-degree pulp to the intrinsic viscosity of the low-polymerization-degree pulp (intrinsic viscosity of high-polymerization-degree pulp/intrinsic viscosity of low-polymerization-degree pulp) is preferably 3.0 or more, more preferably 3.5 to 9.0, and even more preferably 4.0 to 8.5 from the viewpoint of reduction in dissolution variation of an active ingredient.

The mass ratio of the low-polymerization-degree pulp to the high-polymerization-degree pulp is preferably from 1:99 to 99:1 and more preferably from 10:90 to 70:30 from the viewpoint of reduction in dissolution variation of an active ingredient.

By a method comprising steps of: bringing low-polymerization-degree pulp and high-polymerization-degree pulp, such as a pulp mixture containing low-polymerization-degree pulp and high-polymerization-degree pulp, into contact with an alkali metal hydroxide solution to obtain alkali cellulose, and reacting the alkali cellulose with an etherifying agent, mono-batch HPMC (i.e. HPMC produced from one batch) can be obtained.

Examples of each shape of the low-polymerization-degree pulp and the high-polymerization-degree pulp include sheet, chips and powder.

Examples of the alkali metal hydroxide solution include a sodium hydroxide solution and a potassium hydroxide solution. From the viewpoint of cost efficiency, a sodium hydroxide solution is preferred, and an aqueous solution such as an aqueous sodium hydroxide solution and an aqueous potassium hydroxide solution is more preferred. A solution in an alcohol such as ethanol, or a mixed solution in a water-soluble alcohol and water may be used.

Examples of the etherifying agent include a methyl halide such as methyl chloride, methyl bromide and methyl iodide, and an alkylene oxide such as propylene oxide. From the viewpoint of cost efficiency, methyl chloride and propylene oxide are preferred.

Next, the multi-batch HPMC mixture comprising low-viscosity HPMC and high-viscosity HPMC will be described as the HPMC to be used in the composition for a solid preparation. The HPMC mixture is preferably an HPMC mixture containing low-viscosity HPMC and high-viscosity HPMC preferably at 90 to 100% by mass from the viewpoint of reduction in dissolution variation of an active ingredient.

A 2% by mass aqueous solution of the low-viscosity HPMC preferably has a viscosity at 20° C. of 2.0 to 150 mPa·s and more preferably 2.5 to 125 mPa·s from the viewpoint of reduction in dissolution variation of an active ingredient.

The low-viscosity HPMC preferably has a polydispersity of 1.5 to 3.9, more preferably 1.8 to 3.5, and even more preferably 2.0 to 3.0, as determined by absolute molecular weight measurement, from the viewpoint of reduction in dissolution variation of an active ingredient. The low-viscosity HPMC preferably has a weight-average molecular weight (Mw) of 10,000 to 200,000, as determined by absolute molecular weight measurement, from the viewpoint of dissolution control of an active ingredient. The low-viscosity HPMC preferably has a number-average molecular weight (Mn) of 5,000 to 60,000, as determined by absolute molecular weight measurement, from the viewpoint of dissolution control of an active ingredient.

A 2% by mass aqueous solution of the high-viscosity HPMC preferably has a viscosity at 20° C. of 3,500 to 200,000 mPa·s and more preferably 4,000 to 130,000 mPa·s from the viewpoint of reduction in dissolution variation of an active ingredient.

The high-viscosity HPMC preferably has a polydispersity of 1.5 to 3.9, more preferably 1.8 to 3.7, and even more preferably 2.0 to 3.7, as determined by absolute molecular weight measurement, from the viewpoint of reduction in dissolution variation of an active ingredient. The high-viscosity HPMC preferably has a weight-average molecular weight (Mw) of 240,000 to 1,000,000, as determined by absolute molecular weight measurement, from the viewpoint of dissolution control of an active ingredient. The high-viscosity HPMC preferably has a number-average molecular weight (Mn) of 70,000 to 300,000, as determined by absolute molecular weight measurement, from the viewpoint of dissolution control of an active ingredient.

The viscosity at 20° C. of 2% by mass aqueous solution and the polydispersity of the low-viscosity HPMC and those of the high-viscosity HPMC can be determined in the same manner as those for the HPMC to be used in the composition for a solid preparation.

The substitution degrees of methoxy group and hydroxypropoxy group and the average particle sizes of the low-viscosity HPMC and the high-viscosity HPMC are substantially the same as those of the HPMC to be used in the composition for a solid preparation.

The substitution types of the low-viscosity HPMC and the high-viscosity HPMC may be the same or different. They are preferably the same from the viewpoint of suppressing the dissolution of an active ingredient from a sustained-release preparation.

Each of the low-viscosity HPMC and the high-viscosity HPMC may be produced by a known method for producing HPMC. For example, by a method comprising a step of bringing a pulp having a certain intrinsic viscosity into contact with an alkali metal hydroxide solution to obtain alkali cellulose, a step of reacting the alkali cellulose with an etherifying agent to obtain a reaction product, a step of washing and drying the reaction product, and an optional step of pulverizing the washed and dried product, powder HPMC is produced. As the pulp having a certain intrinsic viscosity, for example, low-polymerization-degree pulp may be used in the method for producing mono-batch HPMC to obtain low-viscosity HPMC, whereas high-polymerization-degree pulp may be used in the method for producing mono-batch HPMC to obtain high-viscosity HPMC. The low-viscosity HPMC may also be produced by depolymerization of high-viscosity HPMC through a known HPMC depolymerization method.

The mixing ratio (mass ratio) of the low-viscosity HPMC to the high-viscosity HPMC is, but not limited to, preferably from 5:95 to 95:5, more preferably from 10:90 to 80:20, and even more preferably from 10:90 to 65:35 from the viewpoint of suppressing the dissolution from a sustained-release preparation or reducing the dissolution variation of an active ingredient.

In the composition for a solid preparation, the content of the HPMC is preferably 2% by mass or more and 99.99% by mass or less, more preferably 2% by mass or more and 40% by mass or less, even more preferably 10% by mass or more and 40% by mass or less, especially preferably 10% by mass or more and 30% by mass or less, and particularly preferably not less than 10% by mass and less than 20% by mass from the viewpoint of dissolution control of an active ingredient in a sustained-release preparation.

Commonly, the content of HPMC in a solid preparation (i.e. the content of HPMC in a composition for a solid preparation) is recommended to be 20% by mass or more from the viewpoint of dissolution control of an active ingredient in a sustained-release preparation and reduction in dissolution variation. According to the invention, however, the dissolution can be controlled, and the dissolution variation can be reduced even at a low content of HPMC. Hence, the HPMC content can be less than 20% by mass so that tablets can be made small.

The active ingredient in the composition for a solid preparation may be any active ingredient that can be orally administered. Examples of the active ingredient include drugs used in pharmaceutical products and active ingredients used in foods with nutrient function claims, specifically health foods including foods for specified health use and foods with functional claims.

Examples of the drug used in pharmaceutical products include a drug for the central nervous system, a drugs for the cardiovascular system, a drug for the respiratory system, a drugs for the digestive system, an antibiotic, an antitussive and expectorant, an antihistamine, a antipyretic anti-inflammatory analgesic, a diuretic, an autonomic agent, an antimalarial agent, an antidiarrheal agent, a psychotropic, and vitamins and derivatives thereof.

Examples of the drug for the central nervous system include diazepam, idebenone, naproxen, piroxicam, indomethacin, sulindac, lorazepam, nitrazepam, phenytoin, acetaminophen, ethenzamide, ketoprofen, and chlordiazepoxide.

Examples of the drug for the cardiovascular system include molsidomine, vinpocetine, propranolol, methyldopa, dipyridamole, furosemide, triamterene, nifedipine, atenolol, spironolactone, metoprolol, pindolol, captopril, isosorbide dinitrate, delapril hydrochloride, meclofenoxate hydrochloride, diltiazem hydrochloride, etilefrine hydrochloride, digitoxin, and alprenolol hydrochloride.

Examples of the drug for the respiratory system include amlexanox, dextromethorphan, theophylline, pseudoephedrine, salbutamol, and guaifenesin.

Examples of the drug for the digestive system include a benzimidazole drug having antiulcer action, such as 2-[[3-methyl-4-(2,2,2-trifluoroethoxy)-2-pyridyl]methylsulfinyl] benzimidazole and 5-methoxy-2-[(4-methoxy-3,5-dimethyl-2-pyridyl)methylsulfinyl]benzimidazole; cimetidine; ranitidine; pirenzepine hydrochloride; pancreatin; bisacodyl; and 5-aminosalicylic acid.

Examples of the antibiotic include talampicillin hydrochloride, bacampicillin hydrochloride, cefaclor, and erythromycin.

Examples of the antitussive and expectorant include noscapine hydrochloride, carbetapentane citrate, isoaminile citrate, and dimemorfan phosphate.

Examples of the antihistamine include chlorpheniramine maleate, diphenhydramine hydrochloride, and promethazine hydrochloride.

Examples of the antipyretic anti-inflammatory analgesic include ibuprofen, diclofenac sodium, flufenamic acid, sulpyrine, aspirin, and ketoprofen.

Examples of the diuretic include caffeine.

Examples of the autonomic agent include dihydrocodeine phosphate, dl-methylephedrine hydrochloride, atropine sulfate, acetylcholine chloride, and neostigmine.

Examples of the antimalarial agent include quinine hydrochloride.

Examples of the antidiarrheal agent include loperamide hydrochloride.

Examples of the psychotropic include chlorpromazine.

Examples of the vitamins and derivatives thereof include vitamin A, vitamin B1, fursultiamine, vitamin B2, vitamin B6, vitamin B12, vitamin C, vitamin D, vitamin E, vitamin K, calcium pantothenate, and tranexamic acid.

Examples of the active ingredient used in the health food include the above vitamins and derivatives thereof, minerals, carotenoids, amino acids and derivatives thereof, plant extracts, and health food materials.

Examples of the mineral include calcium, magnesium, manganese, zinc, iron, copper, selenium, chromium, sulfur, and iodine.

Examples of the carotenoid include β-carotene, α-carotene, lutein, cryptoxanthin, zeaxanthin, lycopene, astaxanthin, and Multicarotene.

Examples of the amino acid include acidic amino acids, basic amino acids, neutral amino acids, and acidic amino acid amides.

Examples of the acidic amino acid include aspartic acid and glutamic acid.

Examples of the basic amino acid include lysine, arginine, and histidine.

Examples of the neutral amino acid include linear aliphatic amino acids such as alanine and glycine; branched aliphatic amino acids such as valine, leucine and isoleucine; hydroxyamino acids such as serine and threonine; sulfur-containing amino acids such as cysteine and methionine; aromatic amino acids such as phenylalanine and tyrosine; heterocyclic amino acids such as tryptophan; and imino acids such as proline.

Examples of the acidic amino acid amide include asparagine and glutamine.

Examples of the amino acid derivative include acetylglutamine, acetylcysteine, carboxymethylcysteine, acetyltyrosine, acetylhydroxyproline, 5-hydroxyproline, glutathione, creatine, S-adenosylmethionine, glycylglycine, glycylglutamine, dopa, alanylglutamine, carnitine, and γ-aminobutyric acid.

Examples of the plant extract includes aloe extract, propolis extract, agaricus extract, Panax ginseng extract, ginkgo leaf extract, turmeric extract, curcumin, sprouted brown rice extract, shiitake mycelium extract, Rubus suavissimus extract, sweet Hydrangea leaf extract, Fomes yucatensis extract, sesame extract, garlic extract, maca (Lepidium meyenii) extract, plant worm (Cordyceps sinensis) extract, camomile extract, and red pepper extract.

Examples of the health food material include royal jelly; dietary fibers; proteins; bifidobacteria; lactic acid bacteria; chitosan; yeast; glucosamine; lecithin; polyphenols; cartilage of animals, fish, and shellfish; soft-shelled turtle; lactoferrin; freshwater clams; eicosapentaenoic acid; germanium; enzymes; creatine; carnitine; citric acid; raspberry ketone; coenzyme Q10; methylsulfonylmethane; and soybean peptides bonded with phospholipids.

In the composition for a solid preparation, the content of the active ingredient is, but not limited to, preferably 0.01% by mass to 98% by mass from the viewpoint of pharmaceutical effect or efficacy.

The composition for a solid preparation may contain, in addition to the HPMC and the active ingredient, an optional various additive commonly usable in the field, such as an excipient, a binder, a disintegrant, a lubricant, an aggregation inhibitor, and a solubilizing agent for an active ingredient.

Examples of the excipient include a saccharide such as white soft sugar, lactose, glucose and maltose; a sugar alcohol such as mannitol, sorbitol, erythritol and maltitol; starch; powder cellulose; crystalline cellulose; calcium phosphate; and calcium sulfate.

Examples of the binder include polyvinyl alcohol, polyacrylic acid, polymethacrylic acid, polyvinylpyrrolidone, glucose, white soft sugar, lactose, maltose, dextrin, sorbitol, mannitol, maltitol, macrogols, gum arabic, gelatin, agar, starch, powder cellulose, crystalline cellulose, and low-substituted hydroxypropyl cellulose.

Examples of the disintegrator include low-substituted hydroxypropyl cellulose, carmellose or a salt thereof, croscarmellose sodium, sodium carboxymethyl starch, crospovidone, crystalline cellulose, and crystalline cellulose/carmellose sodium.

Examples of the lubricant and the aggregation inhibitor include talc, magnesium stearate, calcium stearate, colloidal silica, stearic acid, waxes, hardened oil, polyethylene glycol, and sodium benzoate.

Examples of the solubilizing agent for an active ingredient include organic acids such as fumaric acid, succinic acid, malic acid and adipic acid.

The content of such an additive is, but not limited to, preferably 1 to 97.99% by mass from the viewpoint of dissolution control of an active ingredient.

The composition for a solid preparation may be produced by mixing the HPMC, the active ingredient and the optional additive, or by granulating a mixture comprising the HPMC, the active ingredient and the optional additive.

The mixing is not particularly limited, and a commonly used mixer can be used. Examples of the mixer include a V-type mixer, a ribbon mixer, a container mixer, and a tumbler mixer.

The granulation is not particularly limited, and examples thereof include dry granulation and wet granulation. A commonly used granulator may be used for granulation. Examples of the granulator include a dry granulator such as a roller compactor; a high speed mixing granulator; and a fluidized bed granulator.

The mixing time and the granulation time are, but not limited to, typically 1 to 120 minutes.

Next, a solid preparation comprising the composition for a solid preparation will be described. The solid preparation is preferably a solid preparation consisting essentially of the composition for a solid preparation from the viewpoint of reduction in dissolution variation of an active ingredient.

Examples of the dosage form of the solid preparation include a tablet, granules, and fine granules. The dosage form is preferably a tablet from the viewpoint of administration. The granules and the fine granules mean granulated products obtained by granulating the composition for a solid preparation comprising HPMC and an active ingredient, and can also be used as an encapsulated formulation by encapsulation in a capsule.

The solid preparation is preferably a sustained-release preparation from the viewpoint of control of the concentration of an active ingredient dissolved in the blood at a certain level or less, or reduction of the number of administrations. The solid preparation is more preferably a matrix tablet which is easy to handle and most generally used as the sustained-release preparation.

Tablets may be produced, for example, by any one of dry direct tableting, wet blending granulation tableting, fluidized bed granulation tableting, and dry granulation tableting. The dry direct tableting is particularly preferred because it is a simple production process, can simplify production steps, and can greatly reduce the production cost as compared with other tableting methods.

The dry direct tableting is a method comprising a step of tableting a composition for a solid preparation prepared by dry mixing, includes no granulation step, and can simplify the production steps to achieve high productivity.

The wet blending granulation tableting is a method comprising steps of: spraying a binder solution onto a composition for a solid preparation, while applying fluidization movement for granulation with a blade or the like installed in a container to obtain a granulated product; and then drying and tableting the granulated product. This method has an advantage that the granulation time can be shortened.

Examples of the apparatus to be used in the wet blending granulation include a vertical granulator and a high speed mixer.

The fluidized bed granulation tableting is a method comprising steps of: fluidizing powder of a composition for a solid preparation in a fluidized bed, while spraying a binder liquid thereto, so as to allow the powder to aggregate for granulation to obtain a granulated product, and then tableting the granulated product. This method has an advantage that the drying can also be done simultaneously.

Examples of the apparatus to be used in the fluidized bed granulation include a multiplex and a flow coater.

The dry granulation tableting is a method comprising steps of;

compression-granulating a composition for a solid preparation to obtain a compression-granulated product, and tableting the compression-granulated product as a tableting powder. The dry granulation tableting is effective when the active ingredient is susceptible to water or a solvent.

The compression-granulated product may be obtained by roller compression using a compaction granulator such as a roller compactor.

Any of said tableting can be performed in a usual manner.

As described above, the composition for a solid preparation comprising an active ingredient and HPMC having a polydispersity of 4.0 or more, as determined by absolute molecular weight measurement, and a viscosity at 20° C. of 1,500 to 150,000 mPa·s, as determined in a 2% by mass aqueous solution thereof, can be produced, and the solid preparation can also be produced.

EXAMPLES

The invention will next be specifically described with reference to Synthesis Examples, Examples and Comparative Examples. It should not be construed that the invention is limited thereto or thereby.

<Material HPMC to be Used for Production of Composition for Solid Preparation>

The viscosity at 20° C. of 2% by mass aqueous solution, the substitution degree of methoxy group, the substitution degree of hydroxypropoxy group, the average particle size, the molecular weights, and the polydispersity of each of material HPMCs-1 to 9 to be used for production of the composition for a solid preparation in Examples 1 to 11 and Comparative Examples 1 to 5 are shown in Table 1. The material HPMC-8 to be used in Example 11 and the material HPMC-9 to be used in Comparative Example 5 were produced by the methods shown in Synthesis Examples 1 and 2, respectively.

Synthesis Example 1

To 5.2 kg (on dry basis) of powder pulp (low-polymerization-degree pulp) being derived from wood and having an intrinsic viscosity of 380 mL/g and 2.8 kg (on dry basis) of powder pulp (high-polymerization-degree pulp) being derived from linter and having an intrinsic viscosity of 1,880 mL/g in a pressure vessel with an internal stirrer, 11.5 kg of a 49% by mass aqueous sodium hydroxide solution was added to obtain alkali cellulose. The alkali cellulose was reacted with 9.2 kg of methyl chloride and 2.3 kg of propylene oxide to obtain crude HPMC.

The crude HPMC was dispersed in hot water of 90° C., then dehydrated and washed, and dried with a dryer with jacket heating and hot air heating until the residual water content reached 2% by mass or less. The dried product was pulverized with a compaction grinder and then was sieved through a sieve with a mesh size of 355 µm to obtain material HPMC-8.

Synthesis Example 2

Material HPMC-9 was produced in the same procedure as in Synthesis Example 1 except that 8.0 kg (on dry basis) of powder pulp alone being derived from wood and having an intrinsic viscosity of 820 mL/g was used.

"Hypromellose" in the Japanese Pharmacopoeia Seventeenth Edition, and the viscosity was determined with an Ubbelohde-type viscometer in accordance with "Viscosity measurement by capillary tube viscometer" in "Viscosity Determination" of General Tests described in the Japanese Pharmacopoeia Seventeenth Edition.

When an aqueous solution had a viscosity of less than 600 mPa·s, the viscosity determined with an Ubbelohde-type viscometer was regarded as the viscosity at 20° C. of the 2% by mass aqueous solution.

When an aqueous solution had a viscosity of 600 mPa·s or more, the viscosity of the aqueous solution was determined again with MCR301, a rheometer of Anton Paar. More specifically, the viscosity at 20° C. of the 2% by mass aqueous solution was determined comprising steps of: adjusting the temperature of the sample measurement section of the rheometer to 20° C. in advance; pouring a 2% by mass aqueous solution prepared into a CC27 measurement cup (CC27/T200/AL, a cylindrical aluminum container having a diameter of 29 mm and a height of 68 mm) up to a marked line (25 ml); placing a bob cylinder (CC27, a diameter of 26.7 mm and a height of 40.0 mm) at a measurement position in the measurement cup; holding the sample at a shear velocity of 0.01 sec$^{-1}$ for 2 minutes; and then starting the measurement at a shear velocity of 0.4 sec$^{-1}$ to obtain the value at 5 minutes after the start of measurement as the viscosity at 20° C. of the 2% by mass aqueous solution.

<Substitution Degrees of Methoxy Group and Hydroxypropoxy Group>

The substitution degrees of methoxy group and hydroxypropoxy group were determined in accordance with the measurement method of substitution degree of hypromellose in the Japanese Pharmacopoeia Seventeenth Edition.

<Average Particle Size>

The average particle size was determined with a laser diffraction particle size analyzer, MASTERSIZER 3000 (manufactured by Malvern) based on the Fraunhofer diffraction theory by the dry method in conditions of a dispersion pressure of 2 bar and a scattering intensity of 2 to 10%, as a diameter corresponding to the 50% cumulative value on a volume-based cumulative distribution curve.

<Molecular Weight and Polydispersity>

The molecular weight was determined with a GPC-MALLS system including a pump (LC-20AD, manufactured

TABLE 1

| | viscosity (mPa · s) | methoxy (wt %) | hydroxy-propoxy (wt %) | average particle size (µm) | molecular weight Mw × 10$^4$ | molecular weight Mn × 10$^4$ | polydis-persity (Mw/Mn) |
|---|---|---|---|---|---|---|---|
| HPMC-1 | 4.29 | 22.7 | 9.7 | 72.1 | 2.48 | 1.13 | 2.20 |
| HPMC-2 | 97.8 | 23.0 | 9.5 | 70.5 | 12.09 | 4.61 | 2.62 |
| HPMC-3 | 5550 | 23.1 | 9.4 | 75.5 | 30.04 | 9.92 | 3.03 |
| HPMC-4 | 25100 | 23.1 | 9.3 | 71.7 | 44.94 | 13.51 | 3.33 |
| HPMC-5 | 104000 | 23.5 | 9.5 | 74.3 | 72.55 | 29.05 | 2.50 |
| HPMC-6 | 2.98 | 29.0 | 8.8 | 73.5 | 1.80 | 0.92 | 1.96 |
| HPMC-7 | 12100 | 29.3 | 9.1 | 70.8 | 35.73 | 9.70 | 3.69 |
| HPMC-8 | 3910 | 23.7 | 9.6 | 81.7 | 28.65 | 6.82 | 4.20 |
| HPMC-9 | 3060 | 23.4 | 9.4 | 75.8 | 27.12 | 8.07 | 3.36 |

Various physical properties of the material HPMCs were determined by the following methods.

<Viscosity at 20° C. of 2% by Mass Aqueous Solution>

A 2% by mass aqueous solution of HPMC was prepared in accordance with Method I of "Viscosity" under by Shimadzu Corporation), a degasser (DGU-20A3R, manufactured by Shimadzu Corporation), an autosampler (SIL-20A, manufactured by Shimadzu Corporation), a column oven (CTO-20A, manufactured by Shimadzu Corporation), a guard column (SB-G, manufactured by Shoko Science Co., Ltd.), a size-exclusion column (OHpak SB-806M HQ, manufactured by Shoko Science Co., Ltd.), an 18-angle light scattering detector (DAWN Heleos II, manufactured by Wyatt Technologies), and a differential refractometer (Optilab rEx, manufactured by Wyatt Technologies).

HPMC was weighed in a 50-mL screw bottle, subjected to addition of 20 mL of a 0.1 M sodium nitrate ($NaNO_3$) buffer solution under stirring with a magnetic stirrer, and then stirred at room temperature for 1 hour to dissolve the HPMC. Next, the whole was stirred on ice for 1 hour to dissolve the HPMC completely. Then, the solution was allowed to stand at room temperature for 30 minutes to return to room temperature. The concentration of the solution varied depending on the viscosity at 20° C. of a 2% by mass aqueous solution of HPMC. The concentration was adjusted to 0.30% by mass at a viscosity of less than 6 mPa·s, to 0.20% by mass at a viscosity of 6 mPa·s or more and less than 50 mPa·s, to 0.15% by mass at a viscosity of 50 mPa·s or more and less than 400 mPa·s, to 0.10% by mass at a viscosity of 400 mPa·s or more and less than 4,000 mPa·s, to 0.05% by mass at a viscosity of 4,000 mPa·s or more and less than 8,000 mPa·s, to 0.04% by mass at a viscosity of 8,000 mPa·s or more and less than 15,000 mPa·s, to 0.02% by mass at a viscosity of 15,000 mPa·s or more and less than 75,000 mPa·s, and to 0.01% by mass at a viscosity of 75,000 mPa·s or more and not more than 150,000 mPa·s. The prepared solution was filtered through a 0.45-μm membrane filter (DIMIC-13CP, manufactured by Advantec). A standard sample was obtained by adding 2 mL of a 0.1 M sodium nitrate ($NaNO_3$) buffer solution to 5 mg of pullulan (P50, manufactured by Shako Science Co., Ltd.), and filtering the resulting solution through a 0.20-μm membrane filter (DIMIC-13CP, manufactured by Advantec). Each molecular weight of the standard pullulan solution and the HPMC solutions was determined using a 0.1 M sodium nitrate ($NaNO_3$) buffer solution as a mobile phase in measurement conditions of a flow rate of 1.0 mL/min, a column temperature of 40° C., a differential refractometer temperature of 25° C., an injection amount of 200 μL, and a measurement time of 20 minutes.

After the completion of measurement, ASTRA VI (version 6.1.4.25) was used as analysis software to analyze the results by the following method. The dn/dc value of the HPMC was 0.139 mL/g. From the obtained light scattering chromatogram, a peak range was selected, and Detector numbers 5 to 16 of the light scattering detector were used. The molecular weights were calculated using extrapolation (primary) by AUTO Fitting to determine a weight-average molecular weight (Mw), a number-average molecular weight (Mn), and a polydispersity (Mw/Mn). The molecular weight determination results of HPMC were normalized with the determination results of pullulan as the standard sample.

Example 1

Material HPMC-1 as the low-viscosity HPMC and material HPMC-4 as the high-viscosity HPMC were weighed at the mixing ratio shown in Table 2, and then mixed to obtain a HPMC mixture to be used in a composition for a solid preparation. The viscosity at 20° C. of a 2% by mass aqueous solution, the substitution degree of methoxy group, the substitution degree of hydroxypropoxy group, the average particle size, the molecular weights, and the polydispersity of the prepared HPMC mixture are shown in Table 2. Various physical properties were determined in the same manner as those for the material HPMC.

Next, 85 parts by mass of theophylline (manufactured by Shiratori Pharmaceutical) and 15 parts by mass of the prepared HPMC mixture were mixed for 3 minutes to obtain a composition for a solid preparation. The obtained composition for a solid preparation was tableted by dry direct tableting with a single-punch tableting machine in the following tableting conditions to obtain sustained-release tablets.

<Tableting Conditions>
Tableting machine: HANDTAB-200 (manufactured by Ichihashi Seiki)
Tablet size: 480 mg/tablet, a diameter of 12 mm, flat punch
Tableting pressure: 10 kN
<Dissolution Test>

The produced sustained-release tablets were subjected to dissolution test in accordance with Dissolution Test (paddle method) in the Japanese Pharmacopoeia Seventeenth Edition, in the dissolution test conditions below.

At 1, 2, 4, 8, 12, and 16 hours after the start of dissolution test, a test liquid was sampled, and the theophylline amount in the sampled test liquid was determined by measuring the absorbance at a wavelength of 271 nm with a UV detector (UV-1700, manufactured by Shimadzu Corporation). The dissolution test was performed using six tablets. The dissolution percentages of the respective tablets were determined at each time, and the average dissolution percentage at each time was calculated in accordance with the formula below. The results are shown in Table 3.

The relative standard deviation (RSD) of the dissolution percentage at each time was calculated in accordance with the formula below and was used to determine the deviation of the average dissolution percentage in accordance with the formula below. The results are shown in Table 3.

<Dissolution Test Conditions>
Dissolution tester: NTR-6400A (manufactured by Toyama Sangyo)
Test liquid: 900 mL of purified water
Test temperature: 37° C.
Paddle rotation rate: 50 rpm
Number of measured tablets: 6

<Calculation Formula of Average Dissolution Percentage at Each Time>

Average dissolution percentage (%) at each time=average of dissolution percentages of tablets at each time <Calculation Formula of Average Dissolution Percentage Deviation>

Average dissolution percentage variation (%)=(sum of "dissolution percentage variation (%) at each time")/6

The "dissolution percentage variation (%) at each time" is calculated by the following formula.

Dissolution percentage variation (%) at each time= (standard deviation of dissolution percentages at each time/average dissolution percentage at each time)×100

Examples 2 to 11 and Comparative Examples 1 to 5

A composition for a solid preparation was produced in the same manner as in Example 1 except that the low-viscosity HPMC, the high-viscosity HPMC and the mixing ratio were changed in accordance with the description in Table 2. As shown in Table 1, material HPMC-8 alone, material HPMC-3 alone and material HPMC-9 alone were used in Example 11, Comparative Example 1 and Comparative Example 5, respectively. The viscosity at 20° C. of 2% by mass aqueous solution, the substitution degree of methoxy group, the substitution degree of hydroxypropoxy group, the average particle size, the molecular weights, and the polydispersity of HPMC or HPMC mixture contained in each composition for a solid preparation are shown in Table 2.

Sustained-release tablets were produced in the same manner as in Example 1 and were subjected to dissolution test.

The average dissolution percentages at the respective times and the average dissolution percentage variation are shown in Table 3.

TABLE 2

| | HMPC or HPMC mixture (weight ratio) | | properties of HPMC contained in the composition | | | | | | |
|---|---|---|---|---|---|---|---|---|---|
| | low-viscosity HPMC | high-viscosity HPMC | viscosity (mPa·s) | methoxy (wt %) | hydroxy-propoxy (wt %) | Average particle size (μm) | molecular weight Mw × $10^4$ | Mn × $10^4$ | polydispersity (Mw/Mn) |
| Example 1 | HPMC-1 (25) | HPMC-4 (75) | 8990 | 23.0 | 9.4 | 71.4 | 35.98 | 4.78 | 7.53 |
| Example 2 | HPMC-1 (50) | HPMC-5 (50) | 9860 | 23.1 | 9.6 | 72.7 | 37.48 | 3.14 | 11.92 |
| Example 3 | HPMC-1 (42) | HPMC-5 (58) | 16500 | 23.2 | 9.6 | 73.0 | 43.53 | 3.96 | 10.99 |
| Example 4 | HPMC-2 (35) | HPMC-4 (65) | 7300 | 23.1 | 9.4 | 71.2 | 34.50 | 7.42 | 4.65 |
| Example 5 | HPMC-2 (60) | HPMC-5 (40) | 7590 | 23.2 | 9.5 | 71.6 | 35.12 | 6.81 | 5.16 |
| Example 6 | HPMC-2 (38) | HPMC-5 (62) | 25800 | 23.3 | 9.5 | 72.6 | 47.49 | 9.57 | 4.96 |
| Example 7 | HPMC-1 (20) | HPMC-3 (80) | 2450 | 23.0 | 9.5 | 74.5 | 25.66 | 4.89 | 5.25 |
| Example 8 | HPMC-1 (10) | HPMC-5 (90) | 72500 | 23.4 | 9.5 | 74.2 | 62.35 | 14.53 | 4.29 |
| Example 9 | HPMC-1 (65) | HPMC-5 (35) | 2650 | 23.0 | 9.6 | 73.6 | 28.44 | 1.76 | 16.15 |
| Example 10 | HPMC-6 (20) | HPMC-7 (80) | 5420 | 29.2 | 9.0 | 71.1 | 31.79 | 4.23 | 7.52 |
| Example 11 | HPMC-8 (100) | | 3910 | 23.7 | 9.6 | 81.7 | 28.65 | 6.82 | 4.20 |
| Comp.Ex.1 | HPMC-3 (100) | | 5550 | 23.1 | 9.4 | 75.5 | 30.04 | 9.92 | 3.03 |
| Comp.Ex.2 | HPMC-2 (5) | HPMC-5 (95) | 88100 | 23.5 | 9.5 | 73.8 | 64.91 | 27.34 | 2.37 |
| Comp.Ex.3 | HPMC-1 (85) | HPMC-5 (15) | 103 | 22.8 | 9.7 | 73.3 | 12.67 | 1.14 | 11.08 |
| Comp.Ex.4 | HPMC-6 (45) | HPMC-7 (55) | 1300 | 29.2 | 9.0 | 72.2 | 24.74 | 2.00 | 12.35 |
| Comp.Ex.5 | HPMC-9 (100) | | 3060 | 23.4 | 9.4 | 75.8 | 27.12 | 8.07 | 3.36 |

TABLE 3

| | average dissolution percentage (%) | | | | | | Average dissolution variation(%) | sustained release * |
|---|---|---|---|---|---|---|---|---|
| | 1 hour later | 2 hours later | 4 hours later | 8 hours later | 12 hours later | 16 hours later | | |
| Example 1 | 15 | 23 | 34 | 49 | 59 | 69 | 4.2 | A |
| Example 2 | 14 | 21 | 33 | 48 | 60 | 70 | 3.6 | A |
| Example 3 | 15 | 23 | 34 | 49 | 59 | 69 | 4.2 | A |
| Example 4 | 14 | 21 | 31 | 45 | 59 | 74 | 5.0 | A |
| Example 5 | 14 | 22 | 33 | 47 | 60 | 72 | 3.8 | A |
| Example 6 | 13 | 20 | 29 | 41 | 51 | 61 | 4.4 | A |
| Example 7 | 15 | 24 | 37 | 55 | 69 | 83 | 4.4 | A |
| Example 8 | 15 | 22 | 32 | 45 | 53 | 61 | 5.4 | A |
| Example 9 | 17 | 25 | 38 | 59 | 77 | 90 | 4.0 | A |
| Example 10 | 23 | 34 | 49 | 68 | 79 | 88 | 4.3 | A |
| Example 11 | 14 | 22 | 34 | 50 | 66 | 82 | 5.3 | A |
| Comp.Ex.1 | 13 | 20 | 31 | 45 | 60 | 74 | 10.5 | A |
| Comp.Ex.2 | 12 | 18 | 27 | 39 | 47 | 55 | 7.7 | A |
| Comp.Ex.3 | 21 | 35 | 60 | 95 | 99 | 99 | 4.6 | F |

TABLE 3-continued

|  | average dissolution percentage (%) | | | | | | Average dissolution variation(%) | sustained release * |
|---|---|---|---|---|---|---|---|---|
|  | 1 hour later | 2 hours later | 4 hours later | 8 hours later | 12 hours later | 16 hours later | | |
| Comp.Ex.4 | 33 | 47 | 66 | 86 | 96 | 100 | 5.5 | F |
| Comp.Ex.5 | 13 | 21 | 33 | 51 | 68 | 83 | 11.0 | A |

* When it took 12 hours or more for drug dissolution of 85% or more, it is marked as "A". When it took less than 12 hours therefor, it is marked as "F".

It is evident from the results in Table 3 that the sustained-release tablets produced by using the compositions for a solid preparation in Examples 1 to 11 suppressed the drug dissolution over 16 hours. These tablets exhibited low average dissolution percentage variations, indicating that the dissolution variation is small and stable dissolution can be achieved. When HPMCs having substantially the same viscosity values, for example, those in Examples 1 and 2, those in Examples 4 and 5, and those in Examples 7 and 9, are compared, a composition containing HPMC having a larger polydispersity value provided tablets exhibiting a smaller dissolution variation for stable dissolution.

In contrast, the sustained-release tablets produced by using the compositions for a solid preparation in Comparative Examples 1, 2, and 5 exhibited large dissolution variations because the used HPMCs had polydispersity values of less than 4.0.

In the sustained-release tablets produced by using the compositions for a solid preparation in Comparative Examples 3 and 4, because of the used HPMCs having viscosity values at 20° C. of less than 1,500 mPa·s, as determined in a 2% by mass aqueous solution, the average dissolution percentages at 8 hours were 95% and 86%, respectively. These results exhibit that almost all the drug was eluted for about 8 hours when an HPMC content was as small as 15 parts by mass. The effect of suppressing the dissolution in Comparative Examples 3 and 4 is inferior to that in Examples.

The invention claimed is:

1. A composition for a solid preparation, the composition comprising:
   hydroxypropyl methyl cellulose having a substitution degree of methoxy group is 14.0 to 32.0% by mass, a substitution degree of hydroxypropoxy group is 3.0 to 32.0% by mass, and a polydispersity of 4.0 or more, as determined by absolute molecular weight measurement, and a viscosity at 20° C. of 1,500 mPa·s to 150,000 mPa·s, as determined in a 2% by mass aqueous solution thereof; and
   an active ingredient.

2. The composition for a solid preparation according to claim 1, wherein the hydroxypropyl methyl cellulose comprises low-viscosity hydroxypropyl methyl cellulose a substitution degree of methoxy group is 14.0 to 32.0% by mass, a substitution degree of hydroxypropoxy group is 3.0 to 32.0% by mass, and having a viscosity at 20° C. of 2 mPa·s to 150 mPa·s, as determined in a 2% by mass aqueous solution thereof, and high-viscosity hydroxypropyl methyl cellulose having a substitution degree of methoxy group is 14.0 to 32.0% by mass, a substitution degree of hydroxypropoxy group is 3.0 to 32.0% by mass, and a viscosity at 20° C. of 3,500 mPa·s to 200,000 mPa·s, as determined in a 2% by mass aqueous solution.

3. The composition for a solid preparation according to claim 2, wherein a mass ratio of the low-viscosity hydroxypropyl methyl cellulose to the high-viscosity hydroxypropyl methyl cellulose is from 5:95 to 95:5.

4. A solid preparation comprising the composition for a solid preparation according to claim 1.

5. The solid preparation according to claim 4, wherein the solid preparation is a sustained-release preparation.

6. The solid preparation according to claim 4, wherein the solid preparation is in a form of a tablet.

7. A method for producing a tablet, the method comprising steps of:
   dry-mixing the composition for a solid preparation according to claim 1 to obtain a mixture; and
   tableting the mixture to obtain a tablet.

8. A method for producing a tablet, the method comprising steps of:
   granulating a mixture comprising the composition for a solid preparation according to claim 1 to obtain a granulated product; and
   tableting the granulated product to obtain a tablet.

9. The method for producing a tablet according to claim 7, further comprising steps of:
   bringing low-polymerization-degree pulp having an intrinsic viscosity of 300 ml/g to 700 ml/g and high-polymerization-degree pulp having an intrinsic viscosity of 750 ml/g to 2,500 ml/g into contact with an alkali metal hydroxide solution to obtain alkali cellulose; and
   reacting the alkali cellulose with an etherifying agent to obtain the hydroxypropyl methyl cellulose.

10. The method for producing a tablet according to claim 9, wherein a mass ratio of the low-polymerization-degree pulp to the high-polymerization-degree pulp is from 1:99 to 99:1.

11. The method for producing a tablet according to claim 9, wherein a ratio of the intrinsic viscosity of the high-polymerization-degree pulp to the intrinsic viscosity of the low-polymerization-degree pulp is 3.0 or more.

* * * * *